United States Patent
Wybo et al.

(10) Patent No.: US 10,478,097 B2
(45) Date of Patent: *Nov. 19, 2019

(54) NEURAL EVENT DETECTION

(71) Applicant: Innovative Surgical Solutions, LLC, Southfield, MI (US)

(72) Inventors: Christopher Wybo, Highland, MI (US); Darren Scarfe, LaSalle (CA); Aashish Shah, Ann Arbor, MI (US)

(73) Assignee: Innovative Surgical Solutions, Pontiac Trail, MI (US)

( * ) Notice: Subject to any disclaimer, the term of this patent is extended or adjusted under 35 U.S.C. 154(b) by 1452 days.

This patent is subject to a terminal disclaimer.

(21) Appl. No.: 13/965,468

(22) Filed: Aug. 13, 2013

(65) Prior Publication Data

US 2015/0051507 A1 Feb. 19, 2015

(51) Int. Cl.
*A61B 5/11* (2006.01)

(52) U.S. Cl.
CPC .......... *A61B 5/1106* (2013.01); *A61B 5/1109* (2013.01); *A61B 2505/05* (2013.01); *A61B 2562/0204* (2013.01); *A61B 2562/0219* (2013.01); *A61B 2562/0261* (2013.01)

(58) Field of Classification Search
CPC ..... A61B 5/11; A61B 5/1106; A61B 5/04001; A61B 2018/00434
See application file for complete search history.

(56) References Cited

U.S. PATENT DOCUMENTS

| | | |
|---|---|---|
| 3,200,814 A | 8/1965 | Taylor et al. |
| 3,565,080 A | 2/1971 | Ide et al. |
| 3,797,010 A | 3/1974 | Adler et al. |
| 4,155,353 A | 5/1979 | Rea et al. |
| 4,493,327 A | 1/1985 | Bergelson et al. |

(Continued)

FOREIGN PATENT DOCUMENTS

| | | |
|---|---|---|
| EP | 1417000 A2 | 5/2004 |
| EP | 1575010 A1 | 9/2005 |

(Continued)

OTHER PUBLICATIONS

Bartol, Stephen MD, and Laschuk, Maria MD, "Arthroscopic Microscopic Discectomy in Awake Patients: The Effectiveness of Local/Neurolept Anaesthetic", Canadian Spine Society Meeting, Vernon, BC, Canada, Mar. 2002.

(Continued)

*Primary Examiner* — Daniel L Cerioni
*Assistant Examiner* — Yasmeen S Warsi
(74) *Attorney, Agent, or Firm* — Quinn IP Law (57) ABSTRACT

A neural monitoring system for detecting an artificially-induced mechanical muscle response to a stimulus provided within an intracorporeal treatment area includes a mechanical sensor and a processor in communication with the mechanical sensor. The mechanical sensor is configured to be placed in mechanical communication with the muscle and to generate a mechanomyography output signal corresponding to a sensed mechanical movement of the muscle. The processor is configured to receive the mechanomyography output signal from the mechanical sensor and determine a frequency component of the mechanomyography output signal that has a peak magnitude and to detect the occurrence of an artificially-induced mechanical muscle response therefrom.

19 Claims, 6 Drawing Sheets

(56) References Cited

U.S. PATENT DOCUMENTS

| | | |
|---|---|---|
| 4,807,642 A | 2/1989 | Brown |
| 4,817,628 A | 4/1989 | Zealear et al. |
| 4,940,453 A | 7/1990 | Cadwell |
| 4,994,015 A | 2/1991 | Cadwell |
| 5,047,005 A | 9/1991 | Cadwell |
| 5,078,674 A | 1/1992 | Cadwell |
| 5,116,304 A | 5/1992 | Cadwell |
| 5,178,145 A | 1/1993 | Rea |
| 5,284,153 A | 2/1994 | Raymond et al. |
| 5,284,154 A | 2/1994 | Raymond et al. |
| 5,482,038 A | 1/1996 | Ruff |
| 5,566,678 A | 10/1996 | Cadwell |
| 5,593,429 A | 1/1997 | Ruff |
| 5,631,667 A | 5/1997 | Cadwell |
| 5,775,331 A | 7/1998 | Raymond et al. |
| 5,860,939 A | 1/1999 | Wofford et al. |
| 5,888,370 A | 3/1999 | Becker et al. |
| 5,993,630 A | 11/1999 | Becker et al. |
| 5,993,632 A | 11/1999 | Becker et al. |
| 6,030,401 A | 2/2000 | Marino |
| 6,093,205 A | 7/2000 | McLeod et al. |
| 6,181,961 B1 | 1/2001 | Prass |
| 6,183,518 B1 | 2/2001 | Ross et al. |
| 6,206,921 B1 | 3/2001 | Guagliano et al. |
| 6,221,082 B1 | 4/2001 | Marino et al. |
| 6,224,603 B1 | 5/2001 | Marino |
| 6,251,140 B1 | 6/2001 | Marino et al. |
| 6,264,659 B1 | 7/2001 | Ross et al. |
| 6,266,394 B1 | 7/2001 | Marino |
| 6,266,558 B1 | 7/2001 | Gozani et al. |
| 6,280,447 B1 | 8/2001 | Marino et al. |
| 6,287,832 B1 | 9/2001 | Becker et al. |
| 6,290,724 B1 | 9/2001 | Marino |
| 6,312,443 B1 | 11/2001 | Stone |
| 6,324,432 B1 | 11/2001 | Rigaux et al. |
| 6,361,508 B1 | 3/2002 | Johnson et al. |
| 6,368,325 B1 | 4/2002 | McKinley et al. |
| 6,387,070 B1 | 5/2002 | Marino et al. |
| 6,387,130 B1 | 5/2002 | Stone et al. |
| 6,436,143 B1 | 8/2002 | Ross et al. |
| 6,466,817 B1 | 10/2002 | Kaula et al. |
| 6,478,805 B1 | 11/2002 | Marino et al. |
| 6,485,518 B1 | 11/2002 | Cornwall et al. |
| 6,491,626 B1 | 12/2002 | Stone et al. |
| 6,500,128 B2 | 12/2002 | Marino |
| 6,519,319 B1 | 2/2003 | Marino et al. |
| 6,530,930 B1 | 3/2003 | Marino et al. |
| 6,533,797 B1 | 3/2003 | Stone et al. |
| 6,540,747 B1 | 4/2003 | Marino |
| 6,564,078 B1 | 5/2003 | Marino et al. |
| 6,638,281 B2 | 10/2003 | Gorek |
| 6,641,708 B1 | 11/2003 | Becker et al. |
| 6,654,634 B1 | 11/2003 | Prass |
| 6,739,112 B1 | 5/2004 | Marino |
| 6,760,616 B2 | 7/2004 | Hoey et al. |
| 6,764,452 B1 | 7/2004 | Gillespie et al. |
| 6,764,489 B2 | 7/2004 | Ferree |
| 6,802,844 B2 | 10/2004 | Ferree |
| 6,805,668 B1 | 10/2004 | Cadwell |
| 6,807,438 B1 | 10/2004 | Brun Del Re et al. |
| 6,843,790 B2 | 1/2005 | Ferree |
| 6,852,126 B2 | 2/2005 | Ahlgren |
| 6,870,109 B1 | 3/2005 | Villarreal |
| 6,887,248 B2 | 5/2005 | McKinley et al. |
| 6,923,814 B1 | 8/2005 | Hildebrand et al. |
| 6,945,973 B2 | 9/2005 | Bray |
| 6,964,674 B1 | 11/2005 | Matsuura et al. |
| 6,972,199 B2 | 12/2005 | Lebouitz et al. |
| 6,981,990 B2 | 1/2006 | Keller |
| 7,001,432 B2 | 2/2006 | Keller et al. |
| 7,025,769 B1 | 4/2006 | Ferree |
| 7,050,848 B2 | 5/2006 | Hoey et al. |
| 7,072,521 B1 | 7/2006 | Cadwell |
| 7,079,883 B2 | 7/2006 | Marino et al. |
| 7,160,303 B2 | 1/2007 | Keller |
| 7,162,850 B2 | 1/2007 | Marino et al. |
| 7,166,113 B2 | 1/2007 | Arambula et al. |
| 7,175,662 B2 | 2/2007 | Link et al. |
| 7,177,677 B2 | 2/2007 | Kaula et al. |
| 7,207,949 B2 | 4/2007 | Miles et al. |
| 7,214,197 B2 | 5/2007 | Prass |
| 7,214,225 B2 | 5/2007 | Ellis |
| 7,216,001 B2 | 5/2007 | Hacker et al. |
| 7,230,688 B1 | 6/2007 | Villarreal |
| 7,236,832 B2 | 6/2007 | Hemmerling et al. |
| 7,267,691 B2 | 9/2007 | Keller et al. |
| 7,296,500 B1 | 11/2007 | Martinelli |
| 7,320,689 B2 | 1/2008 | Keller |
| 7,338,531 B2 | 3/2008 | Ellis et al. |
| 7,341,590 B2 | 3/2008 | Ferree |
| 7,367,958 B2 | 5/2008 | McBean et al. |
| 7,374,448 B1 | 5/2008 | Jepsen et al. |
| 7,379,767 B2 | 5/2008 | Rea |
| 7,470,236 B1 | 12/2008 | Kelleher et al. |
| 7,485,146 B1 | 2/2009 | Crook et al. |
| 7,522,953 B2 | 4/2009 | Kaula et al. |
| 7,527,629 B2 | 5/2009 | Link et al. |
| 7,527,649 B1 | 5/2009 | Blain |
| 7,553,307 B2 | 6/2009 | Bleich et al. |
| 7,555,343 B2 | 6/2009 | Bleich |
| 7,569,067 B2 | 8/2009 | Keller |
| 7,578,819 B2 | 8/2009 | Bleich et al. |
| 7,582,058 B1 | 9/2009 | Miles et al. |
| 7,583,991 B2 | 9/2009 | Rea |
| 7,611,522 B2 | 11/2009 | Gorek |
| 7,618,423 B1 | 11/2009 | Valentine et al. |
| 7,628,813 B2 | 12/2009 | Link |
| 7,634,315 B2 | 12/2009 | Cholette |
| 7,657,308 B2 | 2/2010 | Miles et al. |
| 7,664,544 B2 | 2/2010 | Miles et al. |
| 7,666,195 B2 | 2/2010 | Kelleher et al. |
| 7,668,588 B2 | 2/2010 | Kovacs |
| 7,691,057 B2 | 4/2010 | Miles et al. |
| 7,693,562 B2 | 4/2010 | Marino et al. |
| 7,708,776 B1 | 5/2010 | Blain et al. |
| 7,713,463 B1 | 5/2010 | Reah et al. |
| 7,722,613 B2 | 5/2010 | Sutterlin et al. |
| 7,722,673 B2 | 5/2010 | Keller |
| 7,738,968 B2 | 6/2010 | Bleich |
| 7,738,969 B2 | 6/2010 | Bleich |
| 7,740,631 B2 | 6/2010 | Bleich et al. |
| 7,766,816 B2 | 8/2010 | Chin et al. |
| 7,776,049 B1 | 8/2010 | Curran et al. |
| 7,776,094 B2 | 8/2010 | McKinley et al. |
| 7,785,248 B2 | 8/2010 | Annest et al. |
| 7,785,253 B1 | 8/2010 | Arambula et al. |
| 7,815,682 B1 | 10/2010 | Peterson et al. |
| 7,819,801 B2 | 10/2010 | Miles et al. |
| 7,828,855 B2 | 11/2010 | Ellis et al. |
| 7,833,251 B1 | 11/2010 | Ahlgren et al. |
| 7,857,813 B2 | 12/2010 | Schmitz et al. |
| 7,862,592 B2 | 1/2011 | Peterson et al. |
| 7,862,614 B2 | 1/2011 | Keller et al. |
| 7,867,277 B1 | 1/2011 | Tohmeh |
| 7,883,527 B2 | 2/2011 | Matsuura et al. |
| 7,887,538 B2 | 2/2011 | Bleich et al. |
| 7,887,568 B2 | 2/2011 | Ahlgren |
| 7,887,595 B1 | 2/2011 | Pimenta |
| 7,892,173 B2 | 2/2011 | Miles et al. |
| 7,901,430 B2 | 3/2011 | Matsuura et al. |
| 7,905,840 B2 | 3/2011 | Pimenta et al. |
| 7,905,886 B2 | 3/2011 | Curran et al. |
| 7,914,350 B1 | 3/2011 | Bozich et al. |
| 7,918,849 B2 | 4/2011 | Bleich et al. |
| 7,918,891 B1 | 4/2011 | Curran et al. |
| 7,920,922 B2 | 4/2011 | Gharib et al. |
| 7,927,337 B2 | 4/2011 | Keller |
| 7,935,051 B2 | 5/2011 | Miles et al. |
| 7,938,830 B2 | 5/2011 | Saadat et al. |
| 7,942,104 B2 | 5/2011 | Butcher et al. |
| 7,942,826 B1 | 5/2011 | Scholl et al. |
| 7,946,236 B2 | 5/2011 | Butcher |
| 7,959,577 B2 | 6/2011 | Schmitz et al. |
| 7,962,191 B2 | 6/2011 | Marino et al. |

(56) References Cited

U.S. PATENT DOCUMENTS

| | | |
|---|---|---|
| 7,963,915 B2 | 6/2011 | Bleich |
| 7,963,927 B2 | 6/2011 | Kelleher et al. |
| 7,981,058 B2 | 7/2011 | Akay |
| 7,981,144 B2 | 7/2011 | Geist et al. |
| 7,991,463 B2 | 8/2011 | Kelleher et al. |
| 8,000,782 B2 | 8/2011 | Gharib et al. |
| 8,005,535 B2 | 8/2011 | Gharib et al. |
| 8,012,212 B2 | 9/2011 | Link et al. |
| 8,016,767 B2 | 9/2011 | Miles et al. |
| 8,016,776 B2 | 9/2011 | Bourget et al. |
| 8,027,716 B2 | 9/2011 | Gharib et al. |
| 8,048,080 B2 | 11/2011 | Bleich et al. |
| 8,050,769 B2 | 11/2011 | Gharib et al. |
| 8,055,349 B2 | 11/2011 | Gharib et al. |
| 8,062,298 B2 | 11/2011 | Schmitz et al. |
| 8,062,300 B2 | 11/2011 | Schmitz et al. |
| 8,062,369 B2 | 11/2011 | Link |
| 8,062,370 B2 | 11/2011 | Keller et al. |
| 8,063,770 B2 | 11/2011 | Costantino |
| 8,068,912 B2 | 11/2011 | Kaula et al. |
| 8,070,812 B2 | 12/2011 | Keller |
| 8,074,591 B2 | 12/2011 | Butcher et al. |
| 8,075,499 B2 | 12/2011 | Nathan et al. |
| 8,075,601 B2 | 12/2011 | Young |
| 8,083,685 B2 | 12/2011 | Fagin et al. |
| 8,083,796 B1 | 12/2011 | Raiszadeh et al. |
| 8,088,163 B1 | 1/2012 | Kleiner |
| 8,088,164 B2 | 1/2012 | Keller |
| 8,090,436 B2 | 1/2012 | Hoey et al. |
| 8,092,455 B2 | 1/2012 | Neubardt et al. |
| 8,092,456 B2 | 1/2012 | Bleich et al. |
| 8,103,339 B2 | 1/2012 | Rea |
| 8,114,019 B2 | 2/2012 | Miles et al. |
| 8,114,162 B1 | 2/2012 | Bradley |
| 8,123,668 B2 | 2/2012 | Annest et al. |
| 8,133,173 B2 | 3/2012 | Miles et al. |
| 8,137,284 B2 | 3/2012 | Miles et al. |
| 8,147,421 B2 | 4/2012 | Farquhar et al. |
| 8,147,551 B2 | 4/2012 | Link et al. |
| 8,165,653 B2 | 4/2012 | Marino et al. |
| 8,167,915 B2 | 5/2012 | Ferree et al. |
| 8,172,750 B2 | 5/2012 | Miles et al. |
| 8,206,312 B2 | 6/2012 | Farquhar |
| 8,255,044 B2 | 8/2012 | Miles et al. |
| 8,255,045 B2 | 8/2012 | Gharib et al. |
| 8,303,515 B2 | 11/2012 | Miles et al. |
| 8,337,410 B2 | 12/2012 | Kelleher et al. |
| 8,343,065 B2 | 1/2013 | Bartol et al. |
| 8,343,079 B2 | 1/2013 | Bartol et al. |
| 8,394,129 B2 | 3/2013 | Morgenstern Lopez et al. |
| 8,500,653 B2 | 8/2013 | Farquhar |
| 8,500,738 B2 | 8/2013 | Wolf, II |
| 8,517,954 B2 | 8/2013 | Batrol et al. |
| 8,535,224 B2 | 9/2013 | Cusimano Reaston et al. |
| 8,538,539 B2 | 9/2013 | Gharib et al. |
| 8,556,808 B2 | 10/2013 | Miles et al. |
| 8,562,539 B2 | 10/2013 | Marino |
| 8,562,660 B2 | 10/2013 | Peyman |
| 8,568,317 B1 | 10/2013 | Gharib et al. |
| 8,591,431 B2 | 11/2013 | Calancie et al. |
| 8,641,638 B2 | 2/2014 | Kelleher et al. |
| 8,731,654 B2 | 5/2014 | Johnson et al. |
| 8,784,330 B1 | 7/2014 | Scholl et al. |
| 8,792,977 B2 | 7/2014 | Kakei et al. |
| 8,864,654 B2 | 10/2014 | Kleiner et al. |
| 8,936,626 B1 | 1/2015 | Tohmeh et al. |
| 8,945,004 B2 | 2/2015 | Miles et al. |
| 8,958,869 B2 | 2/2015 | Kelleher et al. |
| 8,989,855 B2 | 3/2015 | Murphy et al. |
| 8,989,866 B2 | 3/2015 | Gharib et al. |
| 9,014,776 B2 | 4/2015 | Marino et al. |
| 9,014,797 B2 | 4/2015 | Shiffman et al. |
| 9,037,250 B2 | 5/2015 | Kaula et al. |
| 9,066,701 B1 | 6/2015 | Finley et al. |
| 9,084,551 B2 | 7/2015 | Brunnett et al. |
| 9,131,947 B2 | 9/2015 | Ferree |
| 9,192,415 B1 | 11/2015 | Arnold et al. |
| 9,295,396 B2 | 3/2016 | Gharib et al. |
| 9,295,401 B2 | 3/2016 | Cadwell |
| 9,301,711 B2 | 4/2016 | Bartol et al. |
| 9,392,953 B1 | 7/2016 | Gharib |
| 9,446,259 B2 | 9/2016 | Phillips et al. |
| 2001/0031916 A1 | 10/2001 | Bennett et al. |
| 2002/0038092 A1 | 3/2002 | Stanaland et al. |
| 2002/0165590 A1 | 11/2002 | Crowe et al. |
| 2003/0074037 A1 | 4/2003 | Moore et al. |
| 2004/0077969 A1 | 4/2004 | Onda et al. |
| 2004/0186535 A1 | 9/2004 | Knowlton |
| 2004/0230138 A1 | 11/2004 | Inoue et al. |
| 2004/0243018 A1 | 12/2004 | Organ et al. |
| 2005/0075578 A1 | 4/2005 | Gharib et al. |
| 2005/0085741 A1 | 4/2005 | Hoskonen et al. |
| 2005/0102007 A1 | 5/2005 | Ayal et al. |
| 2005/0240086 A1 | 10/2005 | Akay |
| 2005/0245839 A1 | 11/2005 | Stivoric et al. |
| 2005/0280531 A1 | 12/2005 | Fadem et al. |
| 2005/0283204 A1 | 12/2005 | Buhlmann et al. |
| 2006/0020177 A1 | 1/2006 | Seo et al. |
| 2006/0052726 A1 | 3/2006 | Weisz et al. |
| 2006/0135888 A1 | 6/2006 | Mimnagh-Kelleher et al. |
| 2006/0270949 A1 | 11/2006 | Mathie et al. |
| 2007/0038155 A1 | 2/2007 | Kelly, Jr. et al. |
| 2007/0232958 A1 | 10/2007 | Donofrio et al. |
| 2007/0265675 A1 | 11/2007 | Lund et al. |
| 2007/0276270 A1 | 11/2007 | Tran |
| 2008/0051643 A1 | 2/2008 | Park et al. |
| 2008/0058656 A1 | 3/2008 | Costello et al. |
| 2008/0167695 A1 | 7/2008 | Tehrani et al. |
| 2008/0234767 A1 | 9/2008 | Salmon et al. |
| 2008/0287761 A1 | 11/2008 | Hayter et al. |
| 2008/0306363 A1 | 12/2008 | Chaiken et al. |
| 2008/0306397 A1 | 12/2008 | Bonmassar et al. |
| 2008/0312560 A1 | 12/2008 | Jamsen et al. |
| 2008/0312709 A1 | 12/2008 | Volpe et al. |
| 2009/0036747 A1 | 2/2009 | Hayter et al. |
| 2009/0062696 A1 | 3/2009 | Nathan et al. |
| 2009/0069709 A1 | 3/2009 | Schmitz et al. |
| 2009/0069722 A1 | 3/2009 | Flaction et al. |
| 2009/0076336 A1 | 3/2009 | Mazar et al. |
| 2009/0171381 A1 | 6/2009 | Schmitz et al. |
| 2009/0192416 A1 | 7/2009 | Ernst et al. |
| 2009/0228068 A1 | 9/2009 | Buhlmann et al. |
| 2009/0247910 A1 | 10/2009 | Klapper |
| 2009/0306741 A1 | 12/2009 | Hogle et al. |
| 2009/0318779 A1 | 12/2009 | Tran |
| 2010/0137748 A1 | 6/2010 | Sone et al. |
| 2010/0152619 A1 | 6/2010 | Kalpaxis et al. |
| 2010/0152622 A1 | 6/2010 | Teulings |
| 2010/0152623 A1 | 6/2010 | Williams |
| 2010/0168559 A1 | 7/2010 | Tegg et al. |
| 2010/0292617 A1 | 11/2010 | Lei et al. |
| 2011/0004207 A1 | 1/2011 | Wallace et al. |
| 2011/0237974 A1 | 9/2011 | Bartol et al. |
| 2011/0270121 A1 | 11/2011 | Johnson et al. |
| 2012/0053491 A1 | 3/2012 | Nathan et al. |
| 2013/0213659 A1 | 5/2013 | Bartol et al. |
| 2013/0197321 A1 | 8/2013 | Wilson |
| 2013/0204097 A1 | 8/2013 | Rondoni et al. |
| 2013/0253533 A1 | 9/2013 | Bartol et al. |
| 2014/0020178 A1 | 1/2014 | Stashuk et al. |
| 2014/0163411 A1 | 6/2014 | Rea |
| 2014/0275926 A1 | 9/2014 | Scott et al. |
| 2014/0276195 A1 | 9/2014 | Papay et al. |
| 2014/0358026 A1 | 12/2014 | Mashiach et al. |
| 2015/0045783 A1 | 2/2015 | Edidin |
| 2015/0112325 A1 | 4/2015 | Whitman |
| 2015/0230749 A1 | 8/2015 | Gharib et al. |
| 2015/0342521 A1 | 12/2015 | Narita et al. |
| 2015/0342621 A1 | 12/2015 | Jackson, III |
| 2016/0051812 A1 | 2/2016 | Montgomery, Jr. et al. |

(56) References Cited

U.S. PATENT DOCUMENTS

FOREIGN PATENT DOCUMENTS

| EP | 2231003 A1 | 9/2010 |
|---|---|---|
| EP | 2535082 A1 | 12/2012 |
| FR | 2920087 A1 | 2/2009 |
| WO | 0078209 A2 | 12/2000 |
| WO | 2007024147 A1 | 3/2007 |
| WO | WO2014160832 A2 | 10/2014 |
| WO | WO2015171619 A1 | 11/2015 |
| WO | WO2016100340 A1 | 6/2016 |

OTHER PUBLICATIONS

Bartol, Stephen MD, and Laschuk, Maria MD, "Use of Nerve Stimulator to Localize the Spinal Nerve Root During Arthroscopic Discectomy Procedures", Canadian Spine Society Meeting, Vernon, BC, Canada, Mar. 2002.

Begg et al. "Computational Intelligence for Movement Sciences: Neural Networks and Other Emerging Techniques" 2006.

Bourke et al. "A Threshold-Based Fall-Detection Algorithm Using a Bi-Axial Gyroscope Sensor" Medical Engineering and Physics 30 (2008) 84-90.

Fee Jr., James W.; Miller, Freeman; Lennon, Nancy; "EMG Reaction in Muscles About the Knee to Passive Velocity, Acceleration, and Jerk Manipulations"; Alfred I. duPont Hospital for Children, Gait Laboratory, 1600 Rockland Road, Wilmington, DE 19899, United States Journal of Electromyography and Kinesiology 19 (2009) 467-475.

Koceja, D.M., Bernacki, R.H. and Kamen, G., "Methodology for the Quantitative Assessment of Human Crossed-Spinal Reflex Pathways," Medical & Biological Engineering & Computing, Nov. 1991, pp. 603-606, No. 6, US.

Tarata, M.; Spaepen, A.; Puers, R.; "The Accelerometer MMG Measurement Approach, in Monitoring the Muscular Fatigue"; Measurement Science Review; 2001; vol. 1, No. 1.

Murphy, Chris; Campbell, Niall; Caulfield, Brian; Ward, Tomas and Deegan, Catherine; "Micro Electro Mechanical Systems Based Sensor for Mechanomyography", 19th international conference BIOSIGNAL 2008, Brno, Czech Republic.

Nijsen, Tamara M.E.; Aarts, Ronald M.; Arends, Johan B.A.M.; Cluitmans, Pierre J.M.; "Model for Arm Movements During Myoclonic Seizures"; Proceedings of the 29th Annual International Conference of the IEEE EMBS Cite Internationale, Lyon, France Aug. 23-26, 2007

Ohta, Yoichi; Shima, Norihiro; Yabe, Kyonosuke; "Superimposed Mechanomyographic Response at Different Contraction Intensity in Medial Gastrocnemius and Soleus Muscles"; International Journal of Sport and Health Science, vol. 5, 63-70, 2007.

J. Herdmann MD; V. Deletis MD PhD; H.Edmonds PhD; N. Morota MD, Spinal Cord and Nerve Root Monitoring in Spine Surgery and Related Procedures, Spine Journal, Apr. 1, 1996, pp. 879-885, vol. 21.

N. Hollands MB, BS; J. Kostuik. Continuous Electromyographic Moniotring to Detect Nerve Root Injury During Thoracolumbar Scoliosis Surgery, Spine Journal, Nov. 1, 1997, pp. 2547-2550, vol. 22, Issue 21.

C. Harper, J. Daube, Facial Nerve Electromyography and Other Cranial Nerve Monitoring, Journal of Clinical Neurophysiology, May 1998, pp. 206-216, vol. 15, Issue 3.

D. Beck, J. Ben Ecke Jr, Intraoperative Facial Nerve Monitoring Technical Aspects, Official Journal of the American Academy of Otolaryngology—Head and Neck Surgery Foundation, Apr. 27, 1989.

W. Welch MD, R. Rose PhD, J. Balzer PhD, G. Jacobs, MD, Evaluation with evoked and spontaneous electromyography during lumbar instrumentation: a prospective study, Journal of Neurosurgery, Sep. 1997, pp. 397-402, vol. 87, No. 3.

W. Young MD, D. Morledge PhD, W. Martin PhD, K. Park MD, Intraoperative Stimulation of Pedicle Screws: A New Method for Verification of Screw Placement, Journal of Neurosurgery, 1995, pp. 544-547 vol. 44.

K. Sugita MD, S. Kobayashi MD, Technical and instrumental improvements in the surgical treatment of acoustic neurinomas, Journal of Neurosurgery, Dec. 1982, pp. 747-752, vol. 57.

J. Boston, L. Deneault, Sensory evoked potentials: a system for clinical testing and patient monitoring, International Journal of Clinical Monitoring and Computing, 1984, pp. 13-19, Martinus Nijhoff Publishers, Netherlands.

A. Moller, Neuromonitoring in Operations in the Skull Base, The Keio Journal of Medicine, Oct. 1991, pp. 151-159.

J. Maurer, H. Pelster, W. Mann, Intraoperatives Monitoring motorischer Hurnnerven bei Operationen an Hals und Schadelbasis, Laryngo-Rhino-Otol, pp. 561-567, vol. 73.

W. Friedman MD, M. Curran R. Ept, Somatosensory Evoked Potentials after Sequential Extremity Stimulation: A New Method for Improved Monitoring Accuracy, Neurosurgery, 1987, pp. 755-758, vol. 21, No. 5.

R. Gopalan, P. Parker, R. Scott, Microprocessor-Based System for Monitoring Spinal Evoked Potentials During Surgery, IEEE Transactions on Biomedical Engineering, Oct. 1986, pp. 982-985, vol. BME-22, No. 10.

B. Moed MD, B. Ahmad MD, J. Craig MD, G. Jacobson PhD, M. Anders MD, Intraoperative Monitoring with Stimulus-Evoked Electromyography during Placement Iliosacral Screws, The Journal of Bone and Joint Surgery, Apr. 1998, pp. 537-546, vol. 80-A, No. 4, The Journal of Bone and Joint Surgery, Inc.

C. Yingling PhD, J. Gardi PhD, Intraoperative Monitoring of Facial and Cochlear Nerves During Acoustic Neuroma Surgery, Acoustic Neuroma I, Apr. 1992, pp. 413-448, vol. 25, No. 2, Otolaryngologic Clinics of North America.

N. Holland MB, BS, J. Kostuik MD, Continuous Electromyographic Monitoring to Detect Nerve Root Injury During Thoracolumbar Scoliosis Surgery, Spine, 1997, pp. 2547-2550, vol. 22, No. 21, Lippincott-Raven Publishers.

P. Dulguerov, F. Marchal, W. Lehmann, Postparotidectomy Facial Nerve Paralysis: Possible Etiologic Factors and Results with Routine Facial Nerve Monitoring, the Laryngoscope, May 1999, pp. 754-762 vol. 109, Lippincott Williams & Wilkins, Inc. Philadelphia, Pennsylvania.

M. Imai MS, Y. Harada MD, Y. Atsuta MD, Y. Takemitsu MD, T. Iwahara MD, Automated Spinal Cord Monitoring for Spinal Surgery, Paraplegia, 1989, pp. 204-211.

R. Witt, Facial nerve monitoring in parotid surgery: The standard of care?, Otolaryngology—Head and Neck Surgery, Nov. 1998, pp. 468-470, vol. 119, No. 5.

NEURAL EVENT DETECTION

TECHNICAL FIELD

The present invention relates generally to a surgical diagnostic system for detecting the presence of one or more nerves.

BACKGROUND

Traditional surgical practices emphasize the importance of recognizing or verifying the location of nerves to avoid injuring them. Advances in surgical techniques include development of techniques including ever smaller exposures, such as minimally invasive surgical procedures, and the insertion of ever more complex medical devices. With these advances in surgical techniques, there is a corresponding need for improvements in methods of detecting and/or avoiding nerves.

SUMMARY

A neural monitoring system is provided that is capable of detecting an artificially-induced mechanical response of a muscle to stimulus that is provided within an intracorporeal treatment area of a human subject. Additionally, the intracorporeal treatment area generally includes a nerve that innervates the monitored muscle.

The neural monitoring system includes a non-invasive mechanical sensor and a processor. The non-invasive mechanical sensor is configured to be placed in mechanical communication with the muscle and to generate a mechanomyography output signal corresponding to a sensed mechanical movement of the muscle. By non-invasive, it is intended that the mechanical sensor does not require an incision or related surgical procedure to be properly positioned. Instead, it may be held in contact with an external surface of the skin, or may be positioned within a naturally occurring lumen/orifice. The mechanical sensor may generally include an accelerometer, a microphone, a strain gauge, or a piezoelectric device.

The processor is in communication with the mechanical sensor and is configured to receive the mechanomyography output signal from the mechanical sensor.

In one configuration, the processor may determine a frequency component of the mechanomyography output signal that has a peak magnitude relative to one or more adjacent frequencies. The processor may provide an indication to a user if the determined frequency component is within the range of greater than 0 Hz to about 20 Hz. In another configuration, the processor may determine a fundamental frequency of the mechanomyography output signal, and provide an indication to a user if the determined fundamental frequency is within the range of greater than 0 Hz to about 10 Hz. Finally, in still another configuration, the processor may provide an indication to a user if the determined frequency component is greater than an established noise floor by the threshold amount.

The above features and advantages and other features and advantages of the present invention are readily apparent from the following detailed description of the best modes for carrying out the invention when taken in connection with the accompanying drawings.

"A," "an," "the," "at least one," and "one or more" are used interchangeably to indicate that at least one of the item is present; a plurality of such items may be present unless the context clearly indicates otherwise. All numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. Each value within a range and the endpoints of a range are hereby all disclosed as separate embodiment.

DETAILED DESCRIPTION

Figure 1:
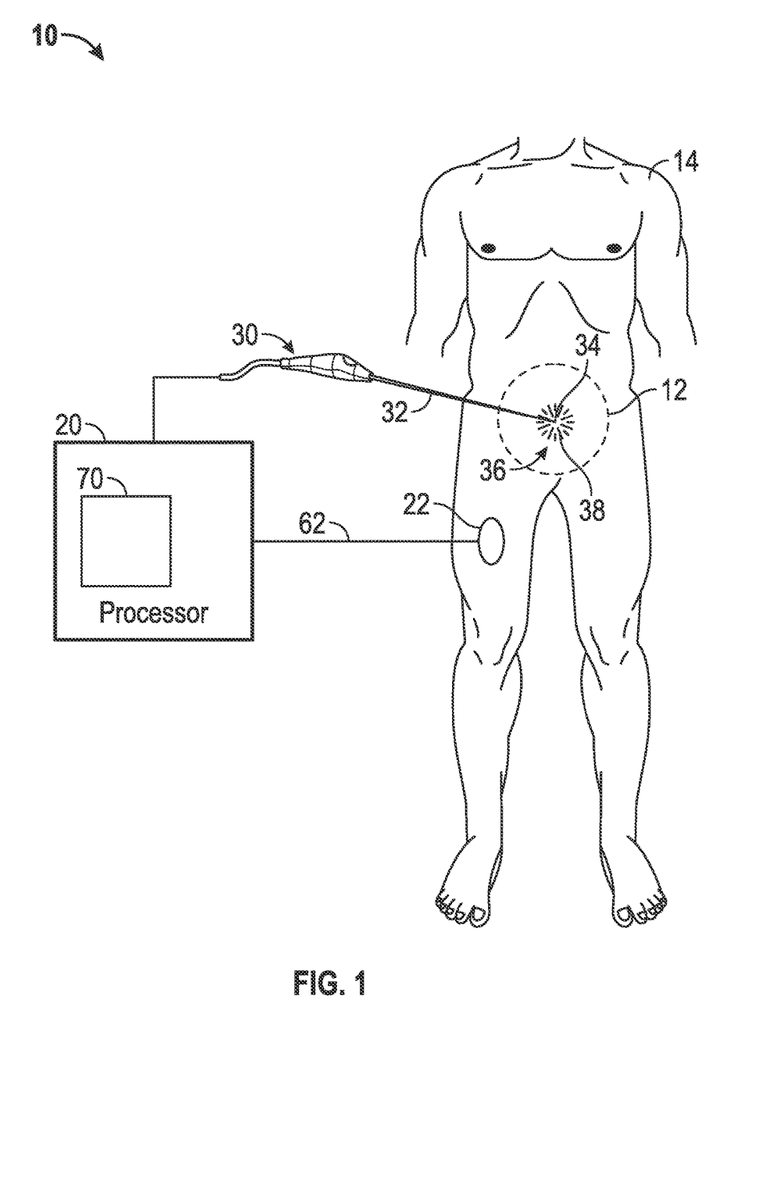
FIG. 1 is a schematic diagram of a neural monitoring system for detecting an artificially-induced mechanical muscle response.

Referring to the drawings, wherein like reference numerals are used to identify like or identical components in the various views, FIG. 1 schematically illustrates a neural monitoring system 10 that may be used to identify the presence of one or more nerves within an intracorporeal treatment area 12 of a subject 14. As will be described in greater detail below, the system 10 may monitor one or more muscles of the subject 14 for a mechanical motion, and may be capable of discriminating an artificially-induced mechanical response of a muscle (also referred to as an "artificially-induced mechanical muscle response") from a subject-intended muscle contraction/relaxation and/or an environmentally caused movement. If an artificially-induced mechanical muscle response is detected during the procedure, the system 10 may provide an indication to a user.

As used herein, an artificially-induced mechanical muscle response refers to a contraction or relaxation of a muscle in response to a stimulus that is not received through natural sensory means (e.g., sight, sound, taste, smell, and touch). Instead, it is a contraction/relaxation of a muscle that is induced by the application of a stimulus directly to a nerve that innervates the muscle. Examples of stimuli that may cause an "artificially-induced" muscle response may include an electrical current applied directly to the nerve or to intracorporeal tissue or fluid immediately surrounding the nerve. In this example, if the applied electrical current is sufficiently strong and/or sufficiently close to the nerve, it may artificially cause the nerve to depolarize (resulting in a corresponding contraction of the muscle innervated by that nerve). Other examples of such "artificial stimuli" may involve mechanically-induced depolarization (e.g., physically stretching or compressing a nerve, such as with a tissue retractor), thermally-induced depolarization (e.g., through ultrasonic cautery), or chemically-induced depolarization (e.g., through the application of a chemical agent to the tissue surrounding the nerve).

During an artificially-induced mechanical muscle response, a muscle innervated by the artificially depolarized nerve may physically contract or relax (i.e., a mechanical response). Such a mechanical reaction may primarily occur along a longitudinal direction of the muscle (i.e., a direction aligned with the constituent fibers of the muscle), though may further result in a respective swelling/relaxing of the muscle in a lateral direction (which may be substantially normal to the skin for most skeletal muscles). This local movement of the muscle during an artificially-induced mechanical muscle response may be measured relative to the position of the muscle when in a non-stimulated state, and is distinguished from other global translations of the muscle The neural monitoring system 10 may include a processor 20 that is in communication with at least one mechanical sensor 22. The mechanical sensor 22 may include, for example, a strain gauge, a force transducer, a position encoder, an accelerometer, a piezoelectric material, or any other transducer or combination of transducers that may convert a physical motion into a variable electrical signal.

Each mechanical sensor 22 may be specially configured to monitor a local mechanical movement of a muscle of the subject 14. For example, each sensor 22 may include a fastening means, such as an adhesive material/patch, that allows the sensor 22 to be adhered, bandaged, or otherwise affixed to the skin of the subject 14 (i.e. affixed on an external skin surface). Other examples of suitable fastening means may include bandages, sleeves, or other elastic fastening devices that may hold the sensor 22 in physical contact with the subject 14. Alternatively, the mechanical sensor 22 (and/or coupled device) may be configured to monitor a local mechanical movement of a muscle by virtue of its physical design. For example, the sensors/coupled devices may include catheters, balloons, bite guards, orifice plugs or endotracheal tubes that may be positioned within a lumen or natural opening of the subject to monitor a response of the lumen or orifice, or of a muscle that is directly adjacent to and/or connected with the lumen or orifice. In one configuration, the mechanical sensor may be a non-invasive device, whereby the term "non-invasive" is intended to mean that the sensor is not surgically placed within the body of the subject (i.e., via cutting of tissue to effectuate the placement). For the purposes of this disclosure, non-invasive sensors may include sensors that are placed within naturally occurring body lumens that are accessible without the need for an incision.

In one configuration, the sensor 22 may include a contact detection device, that may provide an indication if the sensor 22 is in physical contact with the skin of the subject 14. The contact detection device may, for example, include a pair of electrodes that are configured to contact the skin of the subject 14 when the sensor 22 is properly positioned. The sensor 22/contact detection device may then monitor an impedance between the electrodes to determine whether the electrodes are in contact with the skin. Other examples of suitable contact detection devices may include capacitive touch sensors or buttons that protrude slightly beyond the surface of the sensor.

The system 10 may further include one or more elongate medical instruments 30 that are capable of selectively providing a stimulus within the intracorporeal treatment area 12 of the subject 14 (i.e., also referred to as a stimulator 30). For example, in one configuration, the elongate medical instrument 30 may include a probe 32 (e.g., a ball-tip probe, k-wire, or needle) that has an electrode 34 disposed on a distal end portion 36. The electrode 34 may be selectively electrified, at either the request of a user/physician, or at the command of the processor 20, to provide an electrical stimulus 38 to intracorporeal tissue of the subject. In other configurations, the elongate medical instrument 30 may include a dialator, retractor, clip, cautery probe, pedicle screw, or any other medical instrument that may be used in an invasive medical procedure. Regardless of the instrument, if the intended artificial stimulus is an electrical current, the instrument 30 may include a selectively electrifiable electrode 34 disposed at a portion of the instrument that is intended to contact tissue within the intracorporeal treatment area 12 during a procedure.

During a surgical procedure, the user/surgeon may selectively administer the stimulus to intracorporeal tissue within the treatment area 12 to identify the presence of one or more nerve bundles or fibers. For an electrical stimulus 38, the user/surgeon may administer the stimulus, for example, upon depressing a button or foot pedal that is in communication with the system 10, and more specifically in communication with the stimulator 30. The electrical stimulus 38 may, for example, be a discrete pulse (e.g., a step pulse) having a pulse width within the range of about 30 µs to about 500 µs. In other examples, the discrete pulse may have a pulse width within the range of about 50 µs to about 200 µs, or within the range of about 75 µs to about 125 µs. The discrete pulse may be periodically applied at a frequency of, for example, between about 1 Hz and about 10 Hz.

If a nerve extends within a predetermined distance of the electrode 34, the electrical stimulus 38 may cause the nerve to depolarize, resulting in a mechanical twitch of a muscle that is innervated by the nerve (i.e., an artificially-induced mechanical muscle response). In general, the magnitude of the response/twitch may be directly correlated to the distance between the electrode and the nerve, and the magnitude of the stimulus current. In one configuration, a lookup table may be employed by the processor 20 to provide an approximate distance between the electrode and the nerve, given a known stimulus magnitude and a measured mechanical muscle response.

Prior to beginning a surgical procedure, the one or more mechanical sensors 22 may be placed in mechanical communication with one or more muscles of the subject 14. In the present context, a sensor 22 may be in mechanical communication with the muscle if it can physically detect a movement, velocity, acceleration, strain or other physical response of the muscle, either via direct contact with the muscle, or via a mechanical relationship through one or more intermediate materials and/or tissues (e.g., skin and/or subcutaneous tissue).

Figure 2:
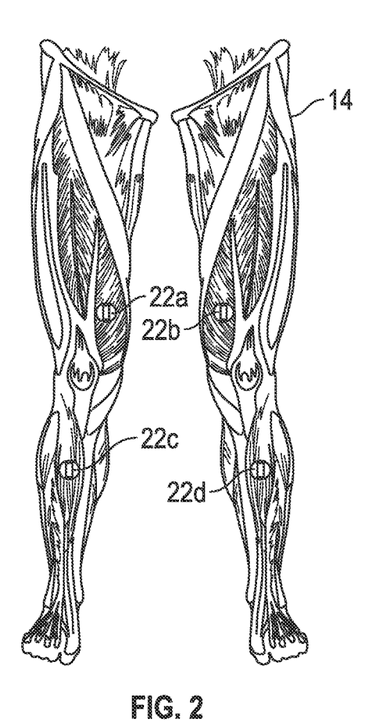
FIG. 2 is a schematic front view of the placement of a plurality of mechanical sensors on the legs of a subject.
Figure 3:
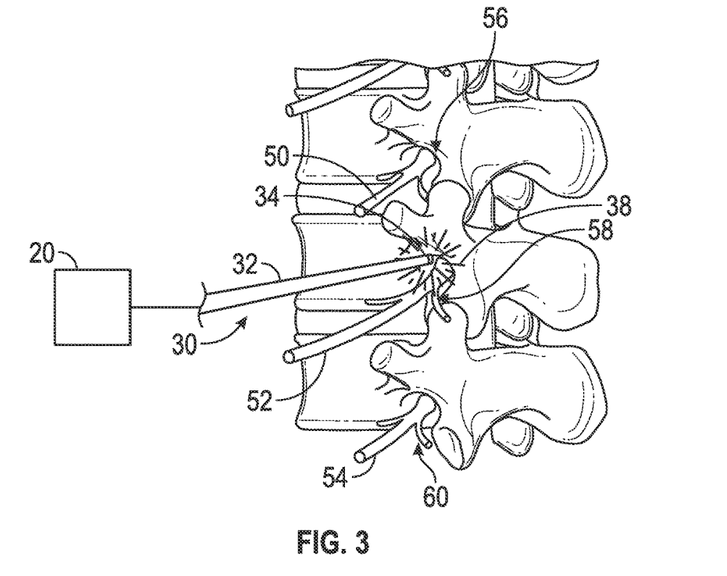
FIG. 3 is a schematic side view of an intracorporeal treatment area including a portion of the lumbar spine.

FIG. 2 illustrates an example of the placement of a plurality of mechanical sensors 22 for a surgical procedure that may occur proximate the L2, L3, and/or L4 vertebrae of the lumbar spine (shown schematically in FIG. 3). The nerves 50, 52 and 54 exiting the L2, L3 and L4 foramen 56, 58, 60 may therefore either lie within the treatment area 12 (i.e., the area surrounding the L2, L3, and/or L4 vertebrae), or may be immediately proximate to this area. Using common anatomical knowledge, the surgeon may understand that damage to these nerves 50, 52, 54 may affect the functioning of the vastus medialis muscles and the tibialis anterior muscles. As such, the surgeon may place mechanical sensors 22a-22d on or near the vastus medialis muscles and the tibialis anterior muscles to guard against inadvertent manipulation of the nerves during the procedure. For example, mechanical sensors 22a and 22b are placed on the vastus medialis muscles, which are innervated by the nerves 50, 52 exiting the L2 and L3 foramen 56, 58, and sensors 22c and 22d are placed on the tibialis anterior muscles, which are innervated by the nerves 54 exiting the L4 foramen 60.

In general, each mechanical sensor 22 may generate a mechanomyography (MMG) output signal (schematically shown at 62) that corresponds to a sensed mechanical movement/response of the adjacent muscle. The MMG output signal 62 may be either a digital or analog signal, and may typically be provided to the processor 20 through either wired or wireless communication means (e.g., through a physical wire, or using radio frequency communication protocols, such as according to IEEE 802.11 or another protocol such as Bluetooth). As a specific signal, the MMG output signal 62 is intended to be separate and distinct from any electrical potentials of the muscle or skin (often referred to as electromyography (EMG) signals). While electrical (EMG) and mechanical (MMG) muscle responses may be related, their relationship is complex, and not easily described (e.g., electrical potentials are very location specific, with a potentially variable electrical potential across the volume of the muscle of interest).

Referring again to FIG. 1, the processor 20 may be in communication with the stimulator 30 and the mechanical sensor 22, and may be configured to receive the MMG output signal 62 from the mechanical sensor 22. The processor 20 may be embodied as one or multiple digital computers, data processing devices, and/or digital signal processors (DSPs), which may have one or more microcontrollers or central processing units (CPUs), read only memory (ROM), random access memory (RAM), electrically-erasable programmable read only memory (EEPROM), a high-speed clock, analog-to-digital (A/D) circuitry, digital-to-analog (D/A) circuitry, input/output (I/O) circuitry, and/or signal conditioning and buffering electronics.

The processor 20 may be configured to automatically perform one or more signal processing algorithms 70 or methods to determine whether a sensed mechanical movement (i.e., via the MMG output signal 62) is representative of an artificially-induced mechanical muscle response or if it is merely a subject-intended muscle movement and/or an environmentally caused movement. These processing algorithms 70 may be embodied as software or firmware, and may either be stored locally on the processor 20, or may be readily assessable by the processor 20.

Figure 4:
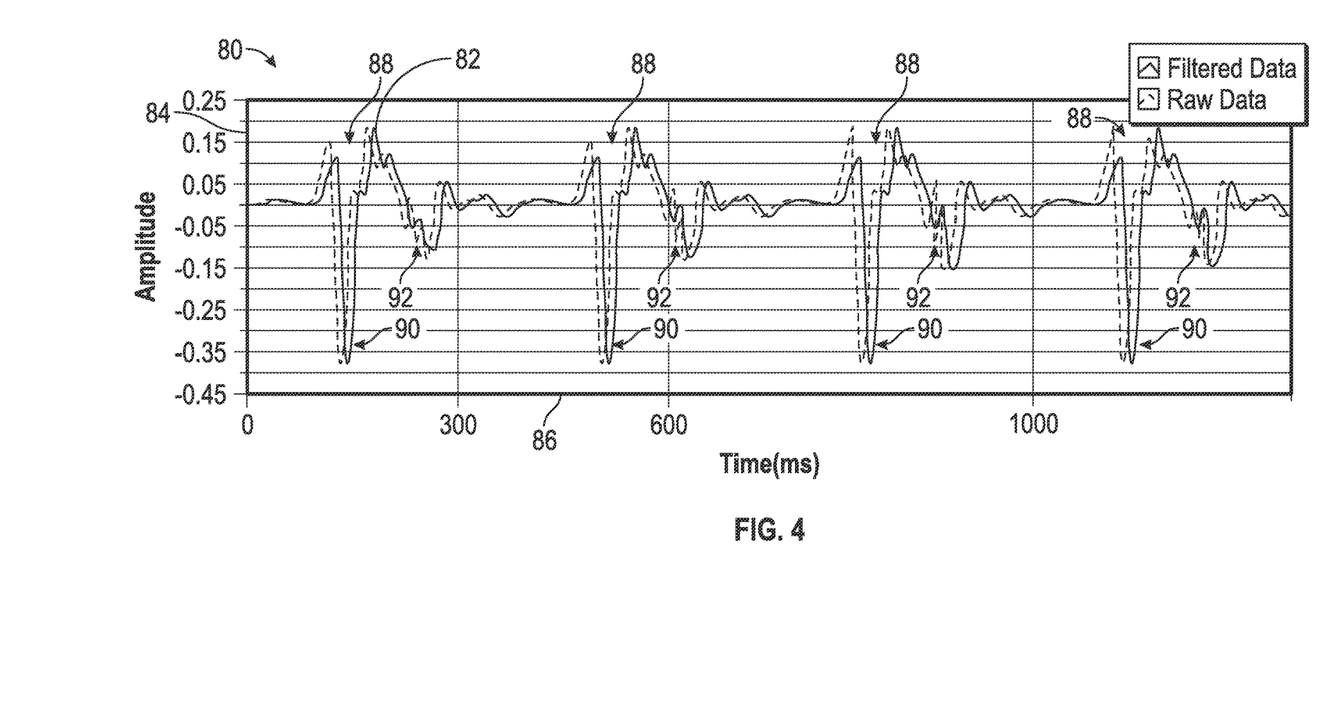
FIG. 4 is a schematic time-domain graph of a mechnomyography output signal in response to a periodic electrical stimulus.

FIG. 4 generally illustrates a graph 80 of an MMG output signal 82 in response to a periodic electrical stimulus 38 provided proximate to a nerve. This MMG output signal 82 may be in response to an electrical stimulus 38 that is provided at about a 3 Hz frequency. As shown, the MMG output signal 82 has an amplitude 84 that varies as a function of time 86 and includes a plurality of generally discrete contraction events 88. Each contraction event 88 may include, for example, an initial response 90, and a plurality of subsequent peaks/valleys 92 that are smaller than the initial response 90.

Figure 5:
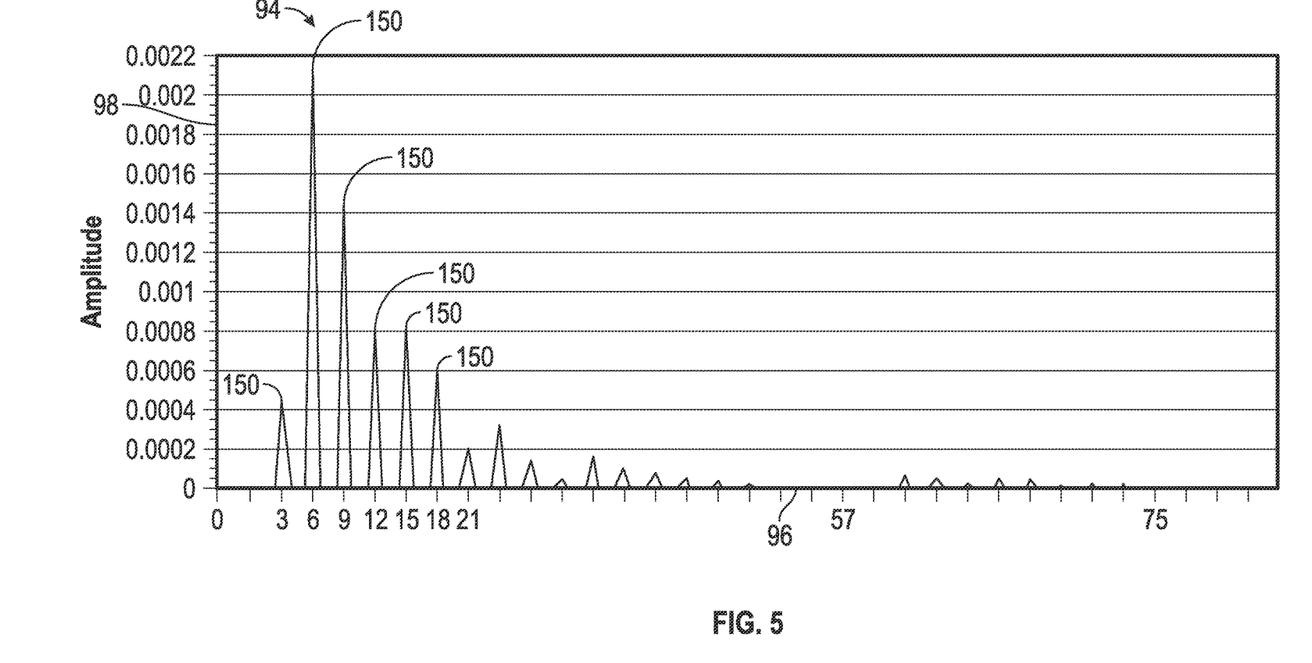
FIG. 5 is a schematic frequency-domain graph of a mechnomyography output signal in response to a periodic electrical stimulus.

While the muscle contractions may be easily represented in the time domain (as generally illustrated by the graph 80 in FIG. 4), they may also be represented in the frequency domain (as generally illustrated by the graph 94 in FIG. 5).

In general, the frequency domain represents a signal as a plurality of discrete frequency components 96, each having a respective magnitude 98. It has been found that an induced muscle response has identifiable frequency content in the range of about 0 Hz to about 50 Hz, with a majority of the signal energy being in the range of about 0 Hz to about 20 Hz.

Figure 6:
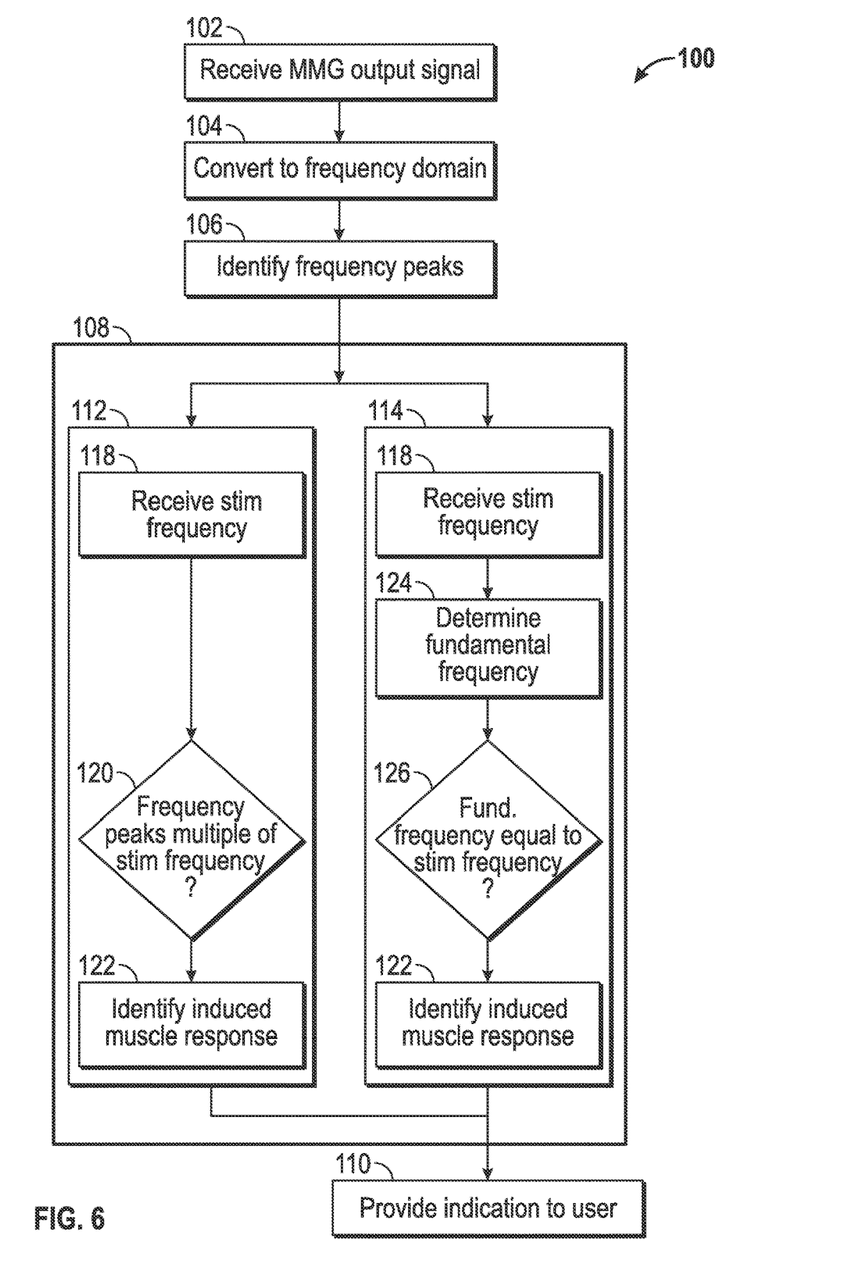
FIG. 6 is a schematic flow diagram of a method for detecting an artificially-induced mechanical muscle response to an electrical stimulus.
Figure 7:
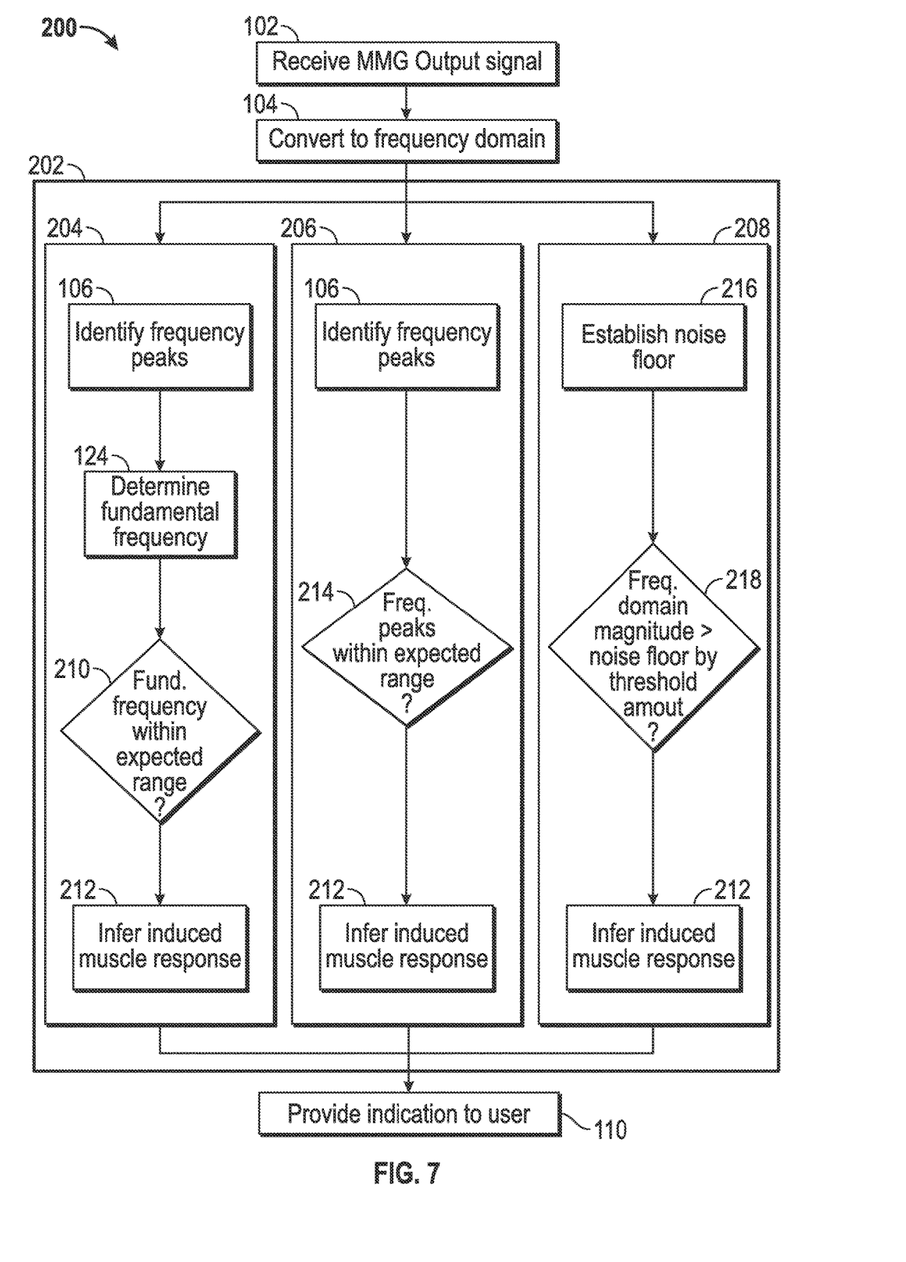
FIG. 7 is a schematic flow diagram of a method of inferring an artificially-induced mechanical muscle response from a free-running mechanomyography output signal.

FIGS. 6 and 7 generally illustrate two methods 100, 200 for detecting an artificially-induced mechanical muscle response, both occurring in the frequency domain. In general, the method 100 provided in FIG. 6 may operate by correlating the MMG output signal 62 in the frequency domain to an applied electrical stimulus 38. Conversely, the method 200 provided in FIG. 7 may operate by solely monitoring the MMG output signal 62 in the frequency domain (i.e., a "free-run" MMG monitoring technique). The two provided methods 100, 200 may be used individually, or may be combined together to provide a more robust detection scheme.

The flow diagram of FIG. 6 generally illustrates a method 100 for detecting an artificially-induced mechanical muscle response to an electrical stimulus 38 that is provided proximate to a nerve. As shown, the method 100 begins when the processor 20 receives the MMG output signal 62 from the mechanical sensor 22 (at step 102). The MMG output signal 62 may be received as a time domain signal, and may potentially be filtered (either by circuitry associated with the mechanical sensor 22 or processor 20, or through digital filtering techniques performed by the processor 20) to remove high frequency noise (such filtering is shown by example in FIG. 4 via the two data traces). For example, in one configuration, the MMG output signal 62 may be filtered using a low pass filter having a cutoff frequency greater than about 200 Hz. In other embodiments, a low pass filter may be used that has a cut off frequency greater than about 50 Hz, or greater than about 20 Hz, or in the range of about 20 Hz to about 50 Hz. In addition to filtering through a low pass filter, the MMG output signal 62 may be further filtered by a high pass filter. In one configuration, the high pass filter may have a cut off frequency that is greater than about 0 Hz though less than about 10 Hz.

After the processor 20 receives the MMG output signal 62 it may convert the received signal 62 from the time domain to the frequency domain (at step 104). Such a conversion may occur using, for example, Fourier Methods (e.g., a Fourier Transform, a Fast Fourier Transform, or a Discrete Fourier Transform), or through other similar methodologies. Once in the frequency domain, the processor 20 may then determine one or more frequency components that have a peak magnitude (at step 106). While numerous methods may be used to detect magnitude peaks, the most basic method includes identifying one or more frequencies that have magnitudes greater than the magnitudes of adjacent frequencies. FIG. 5 generally illustrates at least 6 detectable peaks/peak magnitudes 150. As shown, these peaks 150 correspond to frequencies of about 3 Hz, about 6 Hz, about 9 Hz, about 12 Hz, about 15 Hz, and about 18 Hz.

Referring again to FIG. 6, once the MMG output signal 62 has been converted into the frequency domain (step 104) and a subset of frequencies that correspond to magnitude peaks have been identified (step 106), the processor 20 may determine whether an artificially-induced mechanical muscle response has been sensed by the mechanical sensor 22 (at step 108). If the processor 20 detects such an induced muscle response, then it may provide an indication to a user corresponding to the detected event (at step 110). In one configuration, this indication may include one or more of an illuminated light/LED, a colored light/LED, a textual or symbolic alert on a display device associated with the processor 20, a vibration in the handle of the stimulator, and an audible alert such as a single frequency alert, a multiple frequency alert, and/or an audible natural language alert. Moreover, the indication/alert may include an estimation of the proximity between the electrode and the nerve, such as may be derived using a lookup table as described above, or as explained in U.S. Pat. No. 8,343,065 to Bartol, et al., entitled "NEURAL EVENT DETECTION," which is hereby incorporated by reference in its entirety and for all of the disclosure setforth therein.

Referring back to step 108, in general, there may be two strategies (112, 114) that the processor 20 may employ to determine whether a sensed movement of the mechanical sensor 22 is indicative of an artificially-induced mechanical muscle response. These strategies 112, 114 may both operate by attempting to correlate the detected frequency peaks of the MMG output signal with an attribute of the provided electrical stimulus 38. In practice, the processor 20 may use either of these strategies alone, or it may combine them both together into a single strategy (i.e., either performed concurrently, sequentially, or in combination).

In the first detection strategy 112, the processor 20 may receive an indication of the frequency at which the electrical stimulus 38 is administered (at 118). This frequency indication may either be received directly from the stimulator, or from a register or memory location within the processor itself. In step 120, the processor 20 may examine the frequencies corresponding to magnitude peaks from step 106, and determine whether any of the identified frequencies is an integer multiple of the stimulation frequency. Finally, in step 122 the processor 20 may identify that the sensed response is indicative of an artificially-induced mechanical muscle response if it is determined that one or more of the identified frequencies is an integer multiple of the stimulation frequency. In other configurations, this determination may require that two or more, or even three or more frequencies are integer multiples of the stimulation frequency before an artificially-induced mechanical muscle response is identified.

In the second detection strategy 114, the processor 20 may similarly receive an indication of the frequency at which the electrical stimulus 38 is administered (at 118). In step 124, the processor 20 may examine the frequencies corresponding to magnitude peaks from step 106, and determine a fundamental frequency of the MMG output signal 62. This may be accomplished, for example, by determining a greatest common factor of a plurality of the frequencies where magnitude peaks are detected. This technique applied to the peaks 150 shown in FIG. 6 would result in a fundamental frequency of 3 Hz (i.e., a common factor of 3, 6, 9, 12, 15, and 18). In most cases, the determined fundamental frequency may lie within the range of about 1 Hz to about 10 Hz (i.e., the typical range of simulation frequencies). In step 126, the processor 20 may determine whether the fundamental frequency is either equal to, or an integer multiple of the stimulation frequency, and if so, in step 122, the processor 20 may identify that the sensed response is indicative of an artificially-induced mechanical muscle response.

The method 100 illustrated in FIG. 6 may generally provide a high-confidence indication that a nerve is proximate to the stimulator by correlating an applied stimulus with a monitored response. In some procedures, however, the use of a stimulator may either be impractical, or may not adequately assess the risks posed to nerves that are further away. For example, while stimulated detection may be extremely useful when making a lateral transpsoas approach to the spine, the subsequent use of a mechanical retractor to provide an operating corridor may affect nerves that are outside of the electrically-stimulated detection radius. In this manner it may also be useful to have a free-running detection algorithm that may monitor for artificially-induced mechanical muscle responses that are attributable to, for example, mechanical stimuli. One embodiment of a free-running detection algorithm is shown by the method 200 provided in FIG. 7. While this method 200 may only provide an "inference" of an artificially-induced mechanical muscle response (i.e., due to the absence of a direct correlation), it may be equally valuable in some circumstances.

As shown in FIG. 7, the free-running detection method 200 may be similar to the method 100 of FIG. 6, though may make detection inferences without the knowledge of a stimulation frequency. As shown, the method 200 begins when the processor 20 receives the MMG output signal 62 from the mechanical sensor 22 (at step 102), and subsequently converts the MMG output signal 62 into the frequency domain (step 104). In step 202, the processor 20 may determine (i.e., infer) whether sensed motion detected by the mechanical sensor 22 is indicative of an artificially-induced mechanical muscle response. If the processor 20 does determine that such an induced muscle response has occurred, it may then provide an indication to a user of such an event (at step 110).

Referring back to step 202, in general, there may be three free-run detection strategies (204, 206, 208) that the processor 20 may employ to determine/infer whether a sensed movement of the mechanical sensor 22 is indicative of an artificially-induced mechanical muscle response. These free-run strategies 204, 206, 208 may operate by monitoring the MMG output signal, and attempting to detect signal attributes that may be indicative of an artificially-induced mechanical muscle response. In practice, the processor 20 may use any of these strategies alone, or it may combine two or more of them together into a single strategy (i.e., either performed concurrently, sequentially, or in combination, and/or may be combined with the stimulated techniques of FIG. 6).

In the first free-run detection strategy 204, the processor 20 may first determine one or more frequency components that have a peak magnitude (at step 106). In step 124, the processor 20 may examine the frequencies corresponding to magnitude peaks from step 106, and determine a fundamental frequency of the MMG output signal 62. Finally, the processor 20 may compare the determined fundamental frequency to a range of expected fundamental frequencies for an artificially-induced mechanical muscle response in step 210. Such a range may be, for example, between about 1 Hz and about 10 Hz. If the determined fundamental frequency falls within this range, the processor 20 may infer that the sensed mechanical sensor movement is indicative of an artificially-induced mechanical muscle response (in step 212).

In the second free-run detection strategy 206, the processor 20 may begin by determining one or more frequency components that have a peak magnitude (at step 106). Once the peaks are identified, the processor 20 may compare the peaks to a range of frequencies where frequency content is expected to exist for an artificially-induced mechanical muscle response (in step 214). Such a range may be, for example between about 1 Hz and about 20 Hz. In one configuration, if one or more of the identified peaks are within this range, the processor 20 may infer that the sensed response is indicative of an artificially-induced mechanical muscle response in step 212. In other configurations, the processor 20 may require that two or more, or even three or more of the identified peaks lie within the range before it infers that the sensed response is indicative of an artificially-induced mechanical muscle response.

Finally, in the third free-run detection strategy, 208 the processor 20 does not necessarily need to compute the frequencies corresponding to magnitude peaks, instead, it may first establish a noise floor at step 216, and then it may determine if any of the respective frequency magnitudes exceed the noise floor by a threshold amount (in step 218). If so, the processor 20 may infer that the sensed response is indicative of an artificially-induced mechanical muscle response in step 212.

The noise floor may generally represent the normal background mechanical noise/movement that may be reported by the sensor. It may be a function of the precision of the transducer within the sensor, it may include received electromagnetic radiation, and/or it may include mechanical movement that may be attributable to continuous rhythmic events such as breathing or heart beat. The noise floor may either have a varying magnitude for each frequency, or may generally be a constant value across all frequencies. In this strategy 208, the threshold may be either a fixed amount above the noise floor, or may be a multiple of the noise floor (e.g., a level twice the noise floor, or a level that is set about one or more standard deviations above an average noise level across a period of time).

While the stimulation-based methods/strategies of FIG. 6, as well as the graphs in FIGS. 4 and 5 generally illustrate the present detection schemes using only a single simulation frequency, these methods/strategies may be expanded to the use of multiple stimulation frequencies as well. For example, if a stimulator were to provide an electrical stimulus having both a 3 Hz component and a 5 Hz component, an MMG output signal that is characteristic of an induced muscle response may include peaks at 3 hz, 5 hz, 6 hz, 9 hz, 10 hz, 12 hz, 15 hz within the frequency domain. Also, peaks may be apparent at multiples of the difference in the frequencies (i.e., 2 Hz, 4 Hz, 8 Hz, etc)

In addition to use as a stand alone, or hand-held nerve monitoring apparatus, the present nerve monitoring system 10 and described artificially-induced mechanical muscle response detection algorithms (as described within method 100) may be used by a robotic surgical system, such as described in U.S. patent application Ser. No. 13/428,693, filed Mar. 23, 2012, entitled "ROBOTIC SURGICAL SYSTEM WITH MECHANOMYOGRAPHY FEEDBACK," which is incorporated by reference in its entirety and for all of the disclosure set forth therein. In such a system, the above-described neural monitoring system 10 may be used to provide one or more control signals to a robotic surgical system if an artificially-induced mechanical muscle response is detected. In such an embodiment, the one or more elongate medical instruments 30 described above may be robotically controlled in up to 6 or more degrees of freedom/motion by a robotic controller. This instrument may be configured to perform a surgical procedure within an intracorporeal treatment area at the direction of the robotic controller, and may provide an electrical stimulus 38 in the manner described above. If an artificially-induced mechanical muscle response is detected, the neural monitoring system 10 may instruct the robotic controller (via the provided control signal) to limit the range of available motion of the elongate medical instrument 30 and/or to prevent an actuation of an end effector that may be disposed on the instrument 30 and controllable by the robotic controller.

While the best modes for carrying out the invention have been described in detail, those familiar with the art to which this invention relates will recognize various alternative designs and embodiments for practicing the invention within the scope of the appended claims. It is intended that all matter contained in the above description or shown in the accompanying drawings shall be interpreted as illustrative only and not as limiting.

The invention claimed is:

1. A neural monitoring system for detecting an artificially-induced mechanical response of a muscle to a stimulus provided within an intracorporeal treatment area of a human subject, the intracorporeal treatment area including a nerve that innervates the muscle, the neural monitoring system comprising:
   a non-invasive mechanical sensor configured to be placed in mechanical communication with the muscle and to generate a mechanomyography output signal corresponding to a sensed mechanical movement of the muscle; and
   a processor in communication with the mechanical sensor and configured to:
      receive the mechanomyography output signal from the mechanical sensor;
      determine a frequency component of the mechanomyography output signal, wherein the frequency component has a peak magnitude relative to adjacent frequencies; and
      provide an indication of an artificially induced mechanical muscle response to a user if the determined frequency component has a frequency within the range of greater than 0 Hz to about 20 Hz.

2. The neural monitoring system of claim 1, wherein the processor is further configured to attenuate frequency content of the mechanomyography output signal that is above a cutoff frequency.

3. The neural monitoring system of claim 2, wherein the cutoff frequency is in the range of about 20 Hz to about 50 Hz.

4. The neural monitoring system of claim 1, wherein the processor is configured to determine a frequency component of the mechanomyography output signal that has a peak magnitude by:
   converting the received mechanomyography output signal from a time domain to a frequency domain, wherein the frequency domain is characterized by a plurality of discrete frequencies, each having a corresponding magnitude; and
   identifying the frequency component from the plurality of discrete frequencies that corresponds to a magnitude peak.

5. The neural monitoring system of claim 1, wherein the mechanical sensor includes an accelerometer, a microphone, a strain gauge, or a piezoelectric device.

6. The neural monitoring system of claim 1, wherein the stimulus includes a mechanical manipulation of tissue within the intracorporeal treatment area.

7. A neural monitoring system for detecting an artificially-induced mechanical response of a muscle to a stimulus provided within an intracorporeal treatment area of a human subject, the intracorporeal treatment area including a nerve that innervates the muscle, the neural monitoring system comprising:

a non-invasive mechanical sensor configured to be placed in mechanical communication with the muscle and to generate a mechanomyography output signal corresponding to a sensed mechanical movement of the muscle; and a processor in communication with the mechanical sensor and configured to:
- receive the mechanomyography output signal from the mechanical sensor;
- determine a fundamental frequency of the mechanomyography output signal;
- provide an indication of an artificially-induced mechanical muscle response to a user if the determined fundamental frequency is within the range of greater than 0 Hz to about 10 Hz.

8. The neural monitoring system of claim 7, wherein the processor is further configured to attenuate frequency content of the mechanomyography output signal that is above a cutoff frequency.

9. The neural monitoring system of claim 8, wherein the cutoff frequency is in the range of about 20 Hz to about 50 Hz.

10. The neural monitoring system of claim 7, wherein the processor is configured to determine a fundamental frequency of the mechanomyography output signal by:
- converting the received mechanomyography output signal from a time domain to a frequency domain, wherein the frequency domain is characterized by a plurality of discrete frequencies, each having a corresponding magnitude;
- identifying a subset of the plurality of discrete frequencies wherein each discrete frequency belonging to the subset corresponds to a respective magnitude peak; and
- determining a greatest common factor of the frequencies belonging to the subset.

11. The neural monitoring system of claim 7, wherein the mechanical sensor includes an accelerometer, a microphone, a strain gauge, or a piezoelectric device.

12. The neural monitoring system of claim 7, wherein the stimulus includes a mechanical manipulation of tissue within the intracorporeal treatment area.

13. A neural monitoring system for detecting an artificially-induced mechanical response of a muscle to a stimulus provided within an intracorporeal treatment area of a human subject, the intracorporeal treatment area including a nerve that innervates the muscle, the neural monitoring system comprising:
- a mechanical sensor configured to be placed in mechanical communication with the muscle and to generate a mechanomyography output signal corresponding to a sensed mechanical movement of the muscle; and
- a processor in communication with the mechanical sensor and configured to:
  - receive the mechanomyography output signal from the mechanical sensor;
  - convert the received mechanomyography output signal from a time domain to a frequency domain, wherein the frequency domain is characterized by a plurality of discrete frequencies, each having a corresponding magnitude;
  - provide an indication of an artificially induced mechanical muscle response to a user if the magnitude of at least one of the plurality of discrete frequencies exceeds a threshold, wherein the threshold is above an established noise floor.

14. The neural monitoring system of claim 13, wherein the threshold is a multiple of the noise floor.

15. The neural monitoring system of claim 14, wherein the noise floor has a varying magnitude for each of the plurality of discrete frequencies.

16. The neural monitoring system of claim 14, wherein the processor is configured to indicate that the sensed mechanical movement of the muscle was induced by the provided intracorporeal stimulus if the magnitudes of at least two of the plurality of discrete frequencies exceed the threshold.

17. The neural monitoring system of claim 16, wherein each of the at least two discrete frequencies is an integer multiple of a fundamental frequency.

18. The neural monitoring system of claim 13, wherein the at least one frequency is within the range of greater than 0 Hz to about 20 Hz.

19. The neural monitoring system of claim 13, wherein the stimulus includes a mechanical manipulation of tissue within the intracorporeal treatment area.

* * * * *